United States Patent
Miyama et al.

(10) Patent No.: US 10,537,480 B2
(45) Date of Patent: Jan. 21, 2020

(54) ABSORBENT ARTICLE AND PACKAGING (71) Applicant: UNICHARM CORPORATION, Shikokuchuo-shi, Ehime (JP)

(72) Inventors: Takuya Miyama, Kanonji (JP); Satoru Sakaguchi, Kanonji (JP); Masashi Uda, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 0 days.

(21) Appl. No.: 16/300,060

(22) PCT Filed: Apr. 14, 2017

(86) PCT No.: PCT/JP2017/015252
§ 371 (c)(1),
(2) Date: Nov. 9, 2018

(87) PCT Pub. No.: WO2017/195528
PCT Pub. Date: Nov. 16, 2017

(65) Prior Publication Data
US 2019/0151164 A1 May 23, 2019

(30) Foreign Application Priority Data
May 13, 2016 (JP) .................. 2016-097495

(51) Int. Cl.
*A61F 13/15* (2006.01)
*A61F 13/47* (2006.01)
(Continued)

(52) U.S. Cl.
CPC ........ *A61F 13/47* (2013.01); *A61F 13/15203* (2013.01); *A61F 13/49* (2013.01);
(Continued)

(58) Field of Classification Search
CPC .... A61F 13/47; A61F 13/15203; A61F 13/49; A61F 13/511; A61F 13/514; A61F 13/53;
(Continued)

(56) References Cited

U.S. PATENT DOCUMENTS

| | | | |
|---|---|---|---|
| 2001/0053899 A1* | 12/2001 | Mizutani | A61F 13/51104 604/374 |
| 2004/0170813 A1 | 9/2004 | Digiacomantonio et al. | |
| 2015/0196434 A1* | 7/2015 | Reel | A61F 13/49003 604/372 |

FOREIGN PATENT DOCUMENTS

| | | |
|---|---|---|
| CN | 1329881 A | 1/2002 |
| CN | 103946434 A | 7/2014 |

(Continued)

OTHER PUBLICATIONS

International Search Report in PCT Application No. PCT/JP2017/015252, dated Jul. 4, 2017, 4pp.
(Continued)

*Primary Examiner* — Jacqueline F Stephens
(74) *Attorney, Agent, or Firm* — Hauptman Ham, LLP (57) ABSTRACT

An absorbent article capable of giving a sense of higher security to a user is provided. The absorbent article includes nonwoven fabric. The nonwoven fabric includes organic cotton fibers. The organic cotton fibers form a plurality of fiber lumps in the nonwoven fabric. The fiber lumps are configured to be visible from the outside. The light transmittance of the portion corresponding to the fiber lumps in the nonwoven fabric is lower than the light transmittance of a portion where the fiber lumps are not present in the nonwoven fabric.

6 Claims, 5 Drawing Sheets

(51) Int. Cl.
  *A61F 13/49* (2006.01)
  *A61F 13/511* (2006.01)
  *A61F 13/514* (2006.01)
  *A61F 13/53* (2006.01)
  *A61F 13/551* (2006.01)

(52) U.S. Cl.
  CPC .......... *A61F 13/511* (2013.01); *A61F 13/514* (2013.01); *A61F 13/53* (2013.01); *A61F 13/5513* (2013.01); *A61F 13/15585* (2013.01); *A61F 2013/53035* (2013.01)

(58) Field of Classification Search
  CPC ............ A61F 13/5513; A61F 13/15585; A61F 2013/53035
  USPC ................. 604/367, 369, 374, 375, 376, 377
  See application file for complete search history.

(56) References Cited

FOREIGN PATENT DOCUMENTS

| | | | |
|---|---|---|---|
| EP | 1166731 | A2 | 1/2002 |
| EP | 1166731 | A3 | 1/2002 |
| EP | 2082714 | A1 | 7/2009 |
| JP | 2001-353182 | A | 12/2001 |
| JP | 2002-651 | A | 1/2002 |
| JP | 2002-153510 | A | 5/2002 |
| JP | 2002-159531 | A | 6/2002 |
| JP | 3154532 | U | 10/2009 |
| JP | 2012-116493 | A | 6/2012 |
| JP | 2013-151774 | A | 8/2013 |

OTHER PUBLICATIONS

Supplementary European Search Report in EP Application No. 17795889.9, dated Apr. 18, 2019, 10pp.

Office Action in CN Application No. 201780029703.9, dated Apr. 17, 2019, 16pp.

Office Action in CN Application No. 201780029703.9, dated Oct. 9, 2019, 21pp.

Office Action in JP Application No. 2018-170560, dated Oct. 29, 2019, 7pp.

* cited by examiner

ABSORBENT ARTICLE AND PACKAGING

RELATED APPLICATIONS

The present application is a National Phase of PCT/JP2017/015252, filed Apr. 14, 2017, and claims priority based on Japanese Patent Application No. 2016-097495, filed May, 13, 2016.

TECHNICAL FIELD

The present invention relates to an absorbent article provided with a nonwoven fabric including organic cotton fibers and to a wrapping body in which the absorbent article is packaged.

BACKGROUND ART

Patent Literature 1 discloses an absorbent article provided with a nonwoven fabric including hydrophobic synthetic fibers and hydrophilic fibers. The hydrophilic fibers are natural cellulose fibers such as cotton and rayon. At least a part of the hydrophilic fibers form aggregates that disperse in the sheet. At least a part of the hydrophilic fibers constituting the aggregates is fused to the surface of the hydrophobic fibers.

CITATION LIST

Patent Literature

Patent Literature 1: JP 2002-651 A

SUMMARY OF INVENTION

In recent years, due to the growing awareness of protecting the natural environment and the growing awareness of desiring to use skin friendly materials, users are increasingly interested in naturally derived materials that have been cultivated without agricultural chemicals. In particular, there is an increasing need to use skin-friendly materials for absorbent articles such as disposable diapers used for infants. However, it is difficult for the user to confirm the material of the absorbent article by oneself, and it may be impossible to realize a sense of security for the product.

Therefore, it is desired to provide an absorbent article that can give a user a sense of security.

An absorbent article according to one embodiment includes a nonwoven fabric, in which the nonwoven fabric includes organic cotton fibers, the organic cotton fiber form a plurality of fiber lumps in the nonwoven fabric, the fiber lumps are configured to be visible from the outside, a light transmittance of the portion corresponding to the fiber lumps in the nonwoven fabric is lower than the light transmittance of the portion of the nonwoven fabric where the fiber lumps are not present.

A packaging for an absorbent article according to one embodiment includes the above-described absorbent article and a packaging bag for packaging the absorbent article, in which the packaging bag includes a mark attached to the packaging bag and allowing a user to recognize the use of the organic cotton fibers.

DESCRIPTION OF EMBODIMENTS

According to the present specification and the accompanying drawings, at least the following matters will be disclosed.

An absorbent article including a nonwoven fabric, in which the nonwoven fabric includes organic cotton fibers, the organic cotton fibers form a plurality of fiber lumps in the nonwoven fabric, the fiber lumps are configured to be visible from the outside, a light transmittance of a portion corresponding to the fiber lumps in the nonwoven fabric is lower than the light transmittance of a portion of the nonwoven fabric in which the fiber lumps are not present.

The light transmittance of the portion corresponding to the fiber lumps made of the organic cotton fiber is lower than the light transmittance of the portion around the fiber lumps, so that the user can easily recognize the fiber lumps by sight from the outside. As a result, the user can realize that the organic cotton fiber are used and can further have a sense of security for the product.

According to a preferred embodiment, the plurality of fiber lumps are provided biased toward the surface side of the absorbent article in a thickness direction of the absorbent article. Since the fiber lumps are biased toward the surface side of the absorbent article, the user can more easily recognize the fiber lumps by sight from the outside.

According to a preferred embodiment, the absorbent article includes a colored sheet overlapping the nonwoven fabric, and the colored sheet is provided inside the nonwoven fabric in the thickness direction of the absorbent article. Since the colored sheet is provided inside the nonwoven fabric, it is possible to make the white fiber lumps more noticeable from the outside. As a result, the user can more easily recognize the fiber lumps by sight from the outside.

According to a preferred embodiment, the fiber lumps has a fiber density of 0.075 g/cm3 to 0.2 g/cm3. By increasing the fiber density of the fiber lumps, the fiber lumps can be more noticeable. As a result, the user can more easily recognize the fiber lumps by sight from the outside.

According to a preferred embodiment, the nonwoven fabric further includes synthetic fibers, and a region having a density lower than the density of the fiber lumps and the density of the synthetic fibers is formed around the fiber lumps. Because of the low density region present around the fiber lumps, the fiber lumps can be more noticeable. As a result, the user can more easily recognize the fiber lumps by sight from the outside.

According to a preferred embodiment, the nonwoven fabrics include synthetic fibers, and the organic cotton fibers have an average fiber length shorter than the average fiber length of the synthetic fibers. By increasing the average fiber length of the synthetic fibers 12, it is possible to improve the strength of the nonwoven fabric and the entire absorbent article, and it is possible to decrease fuzzing of the fibers during manufacturing and during use. On the other hand, by decreasing the average fiber length of the organic cotton fibers 10, it is possible to decrease the thermal fusing point among synthetic fibers 12 to achieve appropriate flexibility for the nonwoven fabric and the absorbent article.

According to a preferred embodiment, the organic cotton fibers are not thermally fused to the synthetic fibers. Since the fiber lumps made of the organic cotton fibers are not thermally fused to the synthetic fibers, the boundary between the fiber lumps and the synthetic fibers becomes more noticeable. As a result, the user can more easily recognize the fiber lumps by sight from the outside.

According to a preferred embodiment, a packaging for the absorbent article includes the above-described absorbent article and a packaging bag for packaging the absorbent article, in which the packaging bag includes a mark attached to the packaging bag to allow the user to recognize the use of the organic cotton fibers.

Even when the absorbent article is in a packaged state, the mark for allow the user to recognize the use of the organic cotton fibers is attached to the packaging bag, so that the user can be explicitly inform of the fact that the organic cotton fibers are used. As a result, it is possible to give the user a sense of security guaranteeing gentleness to the skin.

According to an embodiment, the absorbent article includes the mark attached thereto to allow the user to recognize the use of the organic cotton fibers.

Even when the absorbent article is taken out from the packaging bag, the mark that allows the user to recognize the use of the organic cotton fibers is attached to the absorbent article, so that the user can be explicitly informed of the fact the organic cotton fibers are used. As a result, it is possible to give the user a sense of security guaranteeing gentleness to the skin.

Hereinafter, an absorbent article according to an embodiment will be described in detail by referring to the accompanying drawings. The absorbent article of the present invention is, for example, a disposable diaper or a sanitary napkin. In the following embodiment, a disposable diaper is taken as an example and described in detail.

In the drawings, the same or similar parts are indicated by the same or similar reference signs. The drawings are illustrated schematically, and dimensional ratios and other variables differ from those of actual measurements. The actual measurements or the like, therefore, should be determined by referring to the following description. The drawings may include different relationships or ratios of measurements.

Figure 1:
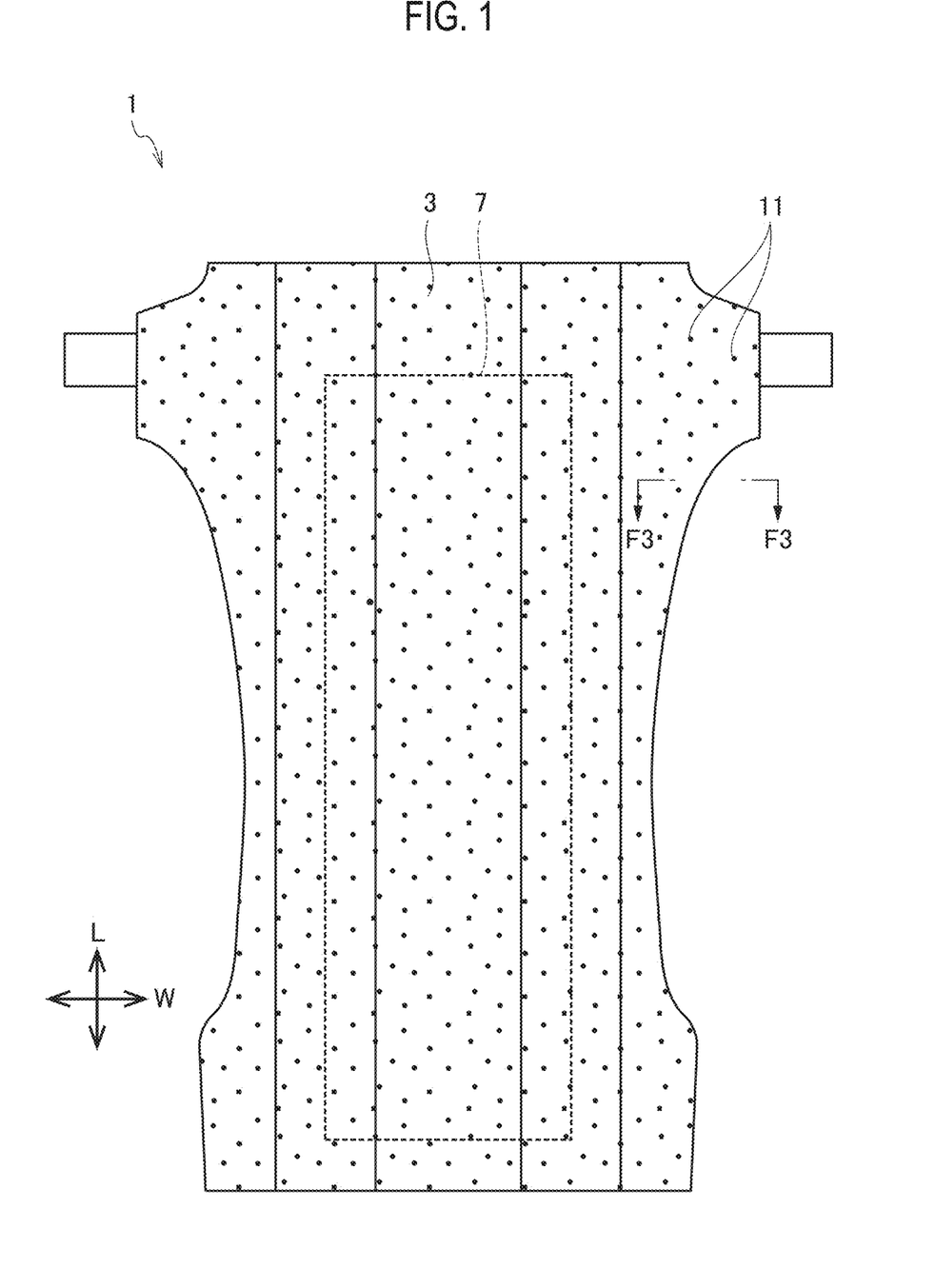
FIG. 1 is a plan view of an absorbent article according to an embodiment.
Figure 2:
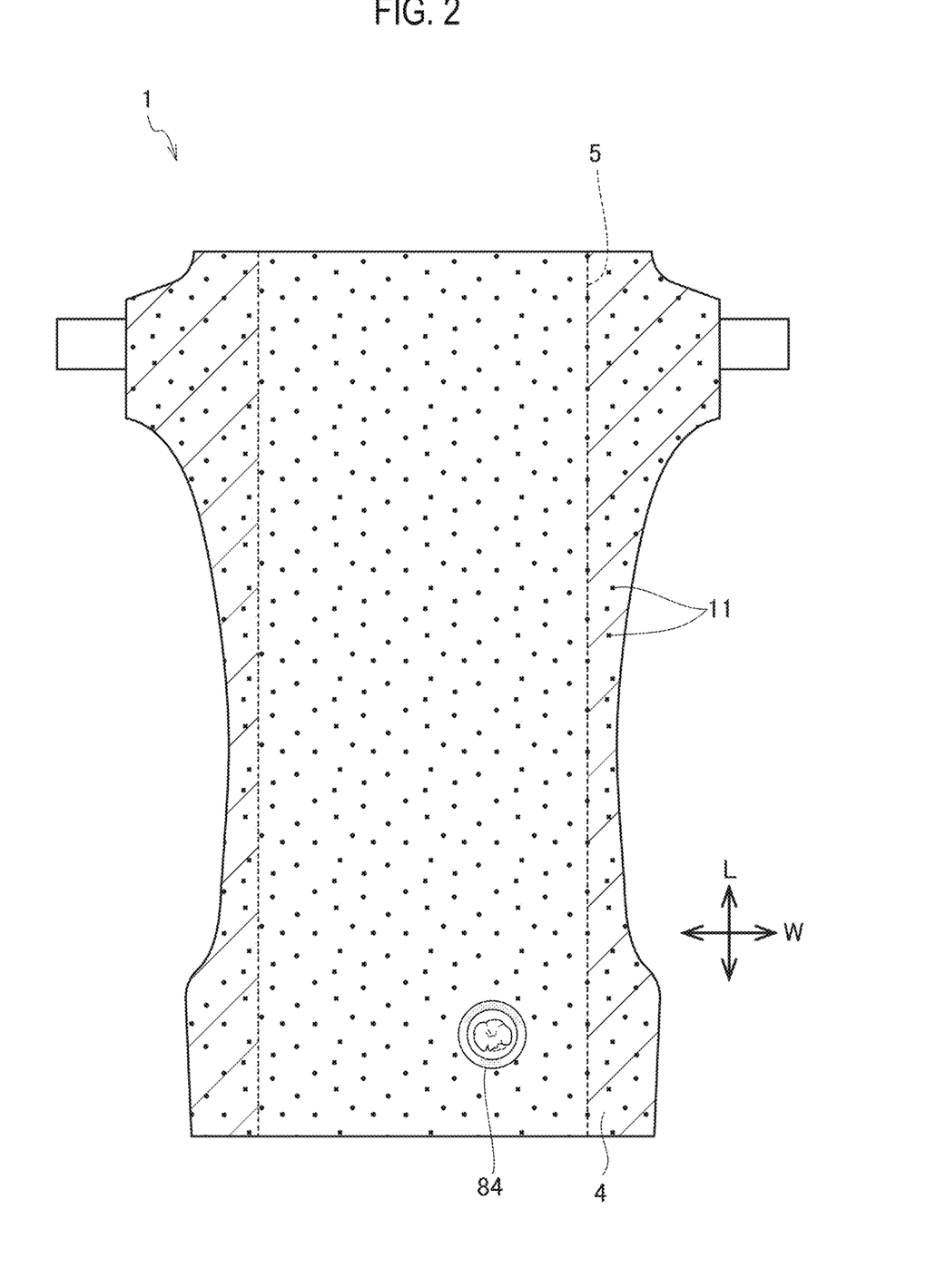
FIG. 2 is a plan view of the absorbent article when seen from the opposite side of FIG. 1.

FIG. 1 is a plan view of an absorbent article according to an embodiment. FIG. 2 is a plan view of the absorbent article when seen from the opposite side of FIG. 1. An absorbent article 1 includes a longitudinal direction L and a width direction W. The longitudinal direction L extends from the front side (ventral side) toward the rear side (dorsal side) of the wearer, or from the rear side toward the front side of the wearer. The width direction W is a direction orthogonal to the longitudinal direction L. Hereinafter, the side facing the skin of the wearer during use may be referred to as the "skin surface side". In addition, the side opposite to the skin of the wearer during use may be referred to as the "non-skin surface side".

The absorbent article 1 has a topsheet 3, a backsheet 4, and an absorber 7. The absorber 7 is disposed between the topsheet 3 and the backsheet 4. The topsheet 3 may be made of a liquid-permeable sheet.

A liquid-impermeable leakage-preventing sheet 5 may be provided between the backsheet 4 and the absorber 7. The leakage-preventing sheet 5 at least covers the absorber 7. The backsheet 4 covers the leakage-preventing sheet 5 and extends to the outside of the leakage-preventing sheet 5. A region of the backsheet 4 not overlapping the leakage-preventing sheet 5 extends from the front end to the rear end in the longitudinal direction L on both outer sides in the width direction W.

Figure 3:
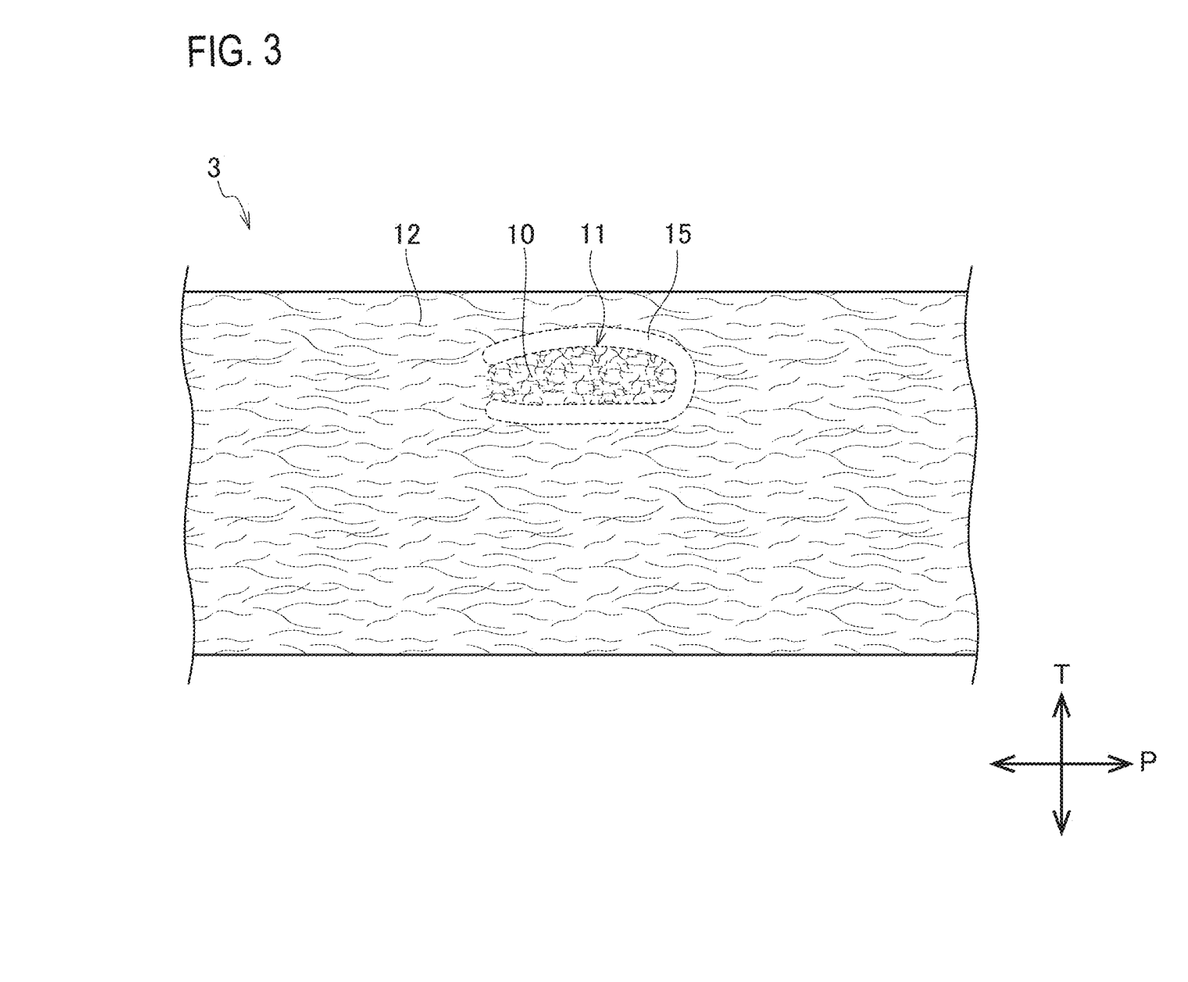
FIG. 3 is a schematic view illustrating a cross section of a nonwoven fabric constituting the absorbent article.

The topsheet 3 and the backsheet 4 are made of a nonwoven fabric. FIG. 3 is a schematic view illustrating a cross section of the topsheet 3 or the backsheet 4. The nonwoven fabric includes organic cotton fibers 10 and synthetic fibers 12. As used herein, "organic cotton" refers to cotton that is certified organic and is so certified in accordance with international standards (standards of each country conforming to CODEX) at the agricultural stage.

The synthetic fibers 12 may be fibers made of a thermoplastic resin. Examples of fibers made of the thermoplastic resin include an olefin resin, a polyester resin, a polyamide resin, and any combination of these resins. The fibers made of a thermoplastic resin may be made hydrophilic by a hydrophilizing agent.

A fineness of the synthetic fibers 12 is not particularly limited, but may be in the range of 1.1 dtex to 8.8 dtex, preferably 1.5 dtex to 4.6 dtex, from the viewpoints of the strength, flexibility, feel of touch, liquid permeability and the like of the nonwoven fabric.

Alternatively, the synthetic fibers may include preferably 10% to 40%, and more preferably 20% to 30% of fibers having the fineness of less than 2.0 dtex among the fibers having the fineness of at least 2.0 dtex. In this case, the synthetic fibers having a short fiber length can be included, while maintaining a long average fiber length. Since the synthetic fibers 12 contain fine count fibers, it is possible to further decrease the fiber lumps of the cotton fibers from falling off from the nonwoven fabric.

The organic cotton fibers 10 form a plurality of fiber lumps 11 in the nonwoven fabric. The organic cotton fibers 10 may have an average fiber length shorter than that of the synthetic fibers 12. As a result, the organic cotton fibers 10 can more easily form the fiber lumps 11 in the nonwoven fabric.

The fiber lumps 11 made of the organic cotton fibers 10 are made visible by sight from the outside. The light transmittance of the portion corresponding to the fiber lumps 11 in the nonwoven fabric is lower than the light transmittance of the portion where the fiber lumps 11 are not present in the nonwoven fabric. In this specification, the light transmittance means the light transmittance of visible light.

The light transmittance of the portion corresponding to the fiber lumps 11 made of the organic cotton fibers 10 is lower than the light transmittance of the portion around the fiber lumps 11, so that the user can easily recognize the fiber lumps 11 by sight from the outside. Thus, the user can realize that the organic cotton fibers 10 are used and can have a sense of higher security for the product.

When the nonwoven fabric is exposed to light and confirmed by the naked eye, the portion corresponding to the fiber lumps 11 made of the organic cotton fibers 10 look whiter than the surrounding area, allowing a difference between the light transmittance of the portion corresponding to the fiber lumps 11 and the light transmittance around the fiber lumps to be confirmed.

As illustrated in FIG. 3, it is preferable that the plurality of fiber lumps 11 is provided so as to be biased toward the surface side of the absorbent article 1 in the thickness direction of the absorbent article 1. It is assumed herein that, if the absorbent article 1 is equally divided into three parts including both layers on the surface sides and a middle layer, and at least 60%, preferably at least 70%, of the plurality of fiber lumps 11 exists on the surface sides (external sides), the fiber lumps 11 are provided biased to the surface sides of the absorbent article 1. The fact that the fiber lumps are present in the layers on the surface side (outer side) means that some of the fiber lumps exist in the surface side (outer side) layer.

Since the plurality of fiber lumps 11 are biased toward the surface side of the absorbent article 1, the user can more easily recognize the fiber lumps by sight from the outside. From the viewpoint of preventing the fiber lumps 11 from falling off from the nonwoven fabric, it is preferable that the fiber lumps 11 are not exposed from the surface of the nonwoven fabric.

In order to confirm the biasing of the fiber lumps 11 in the thickness direction, X-ray CT can be used. Specifically, an X-ray CT (e.g., FLEX-M863 manufactured by BEAM-SENSE Co., Ltd.) is used to photograph the nonwoven fabric including a portion of the fiber lump 11 to be measured from one side to the other side of the nonwoven fabric. Using the image obtained by photographing, it is possible to determine the biasing of the fiber lumps 11 by checking ten fiber lumps 11 in the same nonwoven fabric. It is possible to confirm whether the fiber lumps 11 in the sample after photographing are the fiber lumps 11 of organic cotton fibers by a dyeing method with KayastainQ, which will be described later.

Typically, the nonwoven fabric preferably has a basis weight in the range of 10 g/cm$^2$ to 60 g/cm$^2$. The thickness of the nonwoven fabric is preferably 0.5 mm to 5.0 mm, and more preferably 0.8 mm to 3.5 mm. The thickness of the nonwoven fabric can be measured using a thickness meter (Peacock dial thickness gauge manufactured by OZAKI MFG. CO., LTD.) having a measuring terminal with a measuring pressure of 3 g/cm$^2$ and a diameter of 10 mm. Specifically, the thickness is measured at ten different points of the target nonwoven fabric, and the "thickness" is obtained from the average value.

In the nonwoven fabric having the above thickness, it is preferable to set the weight ratio of organic cotton fibers to synthetic fibers to less than 25%. Under this condition, it is possible to further decrease the falling off of the organic cotton fibers during manufacturing and during use by disposing the fiber lumps 11 biased to the center of the nonwoven fabric in the thickness direction.

The weight ratio of the organic cotton fibers to the synthetic fibers can be calculated by the following method. First, a test piece of a unit area (e.g., 5 cm×5 cm) is taken out from the nonwoven fabric. The organic cotton fibers are taken out from the test piece, and the weight of the taken-out organic cotton fibers is measured. As a result, the weight ratio of the organic cotton fibers to the synthetic fibers can be calculated.

In addition, in extracting the organic cotton fibers from the test piece, it is necessary to first discriminate the difference between synthetic fibers and organic cotton fibers. Whether the fibers in the nonwoven fabric are made of organic cotton fibers or synthetic fibers can be confirmed by the following method First, an amount of KayastainQ (manufactured by Nippon Kayaku Co., Ltd.) equivalent to the amount of the test piece is weighed and dissolved in ion exchanged water (60 to 70 degrees) having a weight 100 times heavier the weight of KayastainQ. This solution is heated and, just before the solution boils, the test piece that has been washed with a neutral detergent, put into the solution. After the solution was boiled for 5 minutes, the test piece was rapidly washed with water and dried. At this point, the fiber lumps are dyed in colors according to the types of fibers. Subsequently, the fiber lumps can be discriminated on the basis of the hues of KayastainQ for various fibers.

The organic cotton fibers 10 included in the nonwoven fabric preferably have an average fiber length shorter than the average fiber length of the synthetic fibers 12 and/or have a fineness smaller than the fineness of the synthetic fibers 12. By increasing the average fiber length of the synthetic fibers 12 and/or increasing the fineness of the synthetic fibers 12, it is possible to improve the strength of the entire nonwoven fabric and decrease fuzzing of the fibers during manufacturing and during use. On the other hand, by decreasing the average fiber length of the organic cotton fibers 10 and/or decreasing the fineness of the organic cotton fibers 10, it is possible to decrease the thermal fusing point among the synthetic fibers 12 and achieve moderate flexibility as a nonwoven fabric.

It is assumed that the "average fiber length" refers to the average fiber length measured according to "A7.1.1 A method (standard method): A method of measuring the length of individual fibers on a glass plate with scale" in "A7.1 Measurement of fiber length" of Annex A, JIS L 1015: 2010. The above method corresponds to the test method equivalent to ISO 6989 issued in 1981.

FIG. 3 is a cross section of a single layer nonwoven fabric constituting the topsheet 3 or the backsheet 4. Alternatively, the topsheet 3 or the backsheet 4 may have a multilayered structure in which a plurality of nonwoven fabrics are layered.

Figure 4:
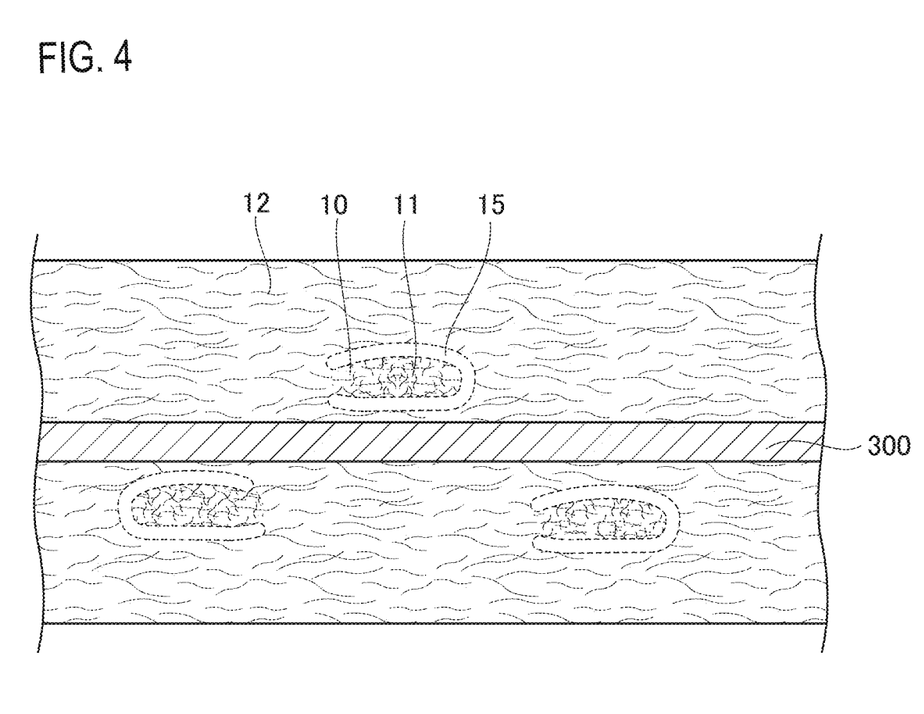
FIG. 4 is a schematic view illustrating a cross section of the absorbent article according to the embodiment.

FIG. 4 illustrates a cross section of a part of the absorbent article (e.g., along line F3-F3 of FIG. 1). The absorbent article 1 preferably includes a colored sheet 300 overlapping a nonwoven fabric constituting the topsheet 3 and/or the backsheet 4. The colored sheet 300 is provided inside the nonwoven fabric constituting the topsheet 3 and/or the backsheet 4 in the thickness direction of the absorbent article 1. Since the colored sheet 300 is provided inside the nonwoven fabric including the organic cotton fibers 10, it is possible to make the white fiber lumps 11 more noticeable. Thus, the user can more easily recognize the fiber lumps 11 by sight from the outside.

The fiber density of the fiber lumps 11 made of the organic cotton fibers 10 is preferably 0.075 g/cm3 to 0.2 g/cm3. By increasing the fiber density of the fiber lumps 11, the fiber lumps 11 can be more noticeable. Thus, the user can more easily recognize the fiber lumps 11 by sight from the outside.

Also, from the viewpoint of making the fiber lumps 11 be noticeable, the fiber density of the fiber lumps 11 is preferably larger than the fiber density of the synthetic fibers 12 by at least 0.02 g/cm3.

As illustrated in FIGS. 3 and 4, it is preferable that a region 15 having a density smaller than the density of the fiber lumps 11 and the density of the synthetic fibers 12 is formed around the individual fiber lumps 11. The presence of the low-density region 15 around individual fiber lumps 11 makes the fiber lumps 11 be more noticeable. Thus, the user can more easily recognize the fiber lumps 11 by sight from the outside.

Preferably, the organic cotton fibers 10 are not thermally fused to the synthetic fibers 12. Since the fiber lumps 11 made of the organic cotton fibers 10 are not thermally fused to the synthetic fibers 12, the boundary between the fiber lump 11 and the synthetic fiber 12 becomes more noticeable. Thus, the user can more easily recognize the fiber lumps 11 by sight from the outside.

Whether the fiber lumps 11 in the nonwoven fabric are made of organic cotton fibers or synthetic fibers can be determined by the above method using KayastainQ.

Figure 5:
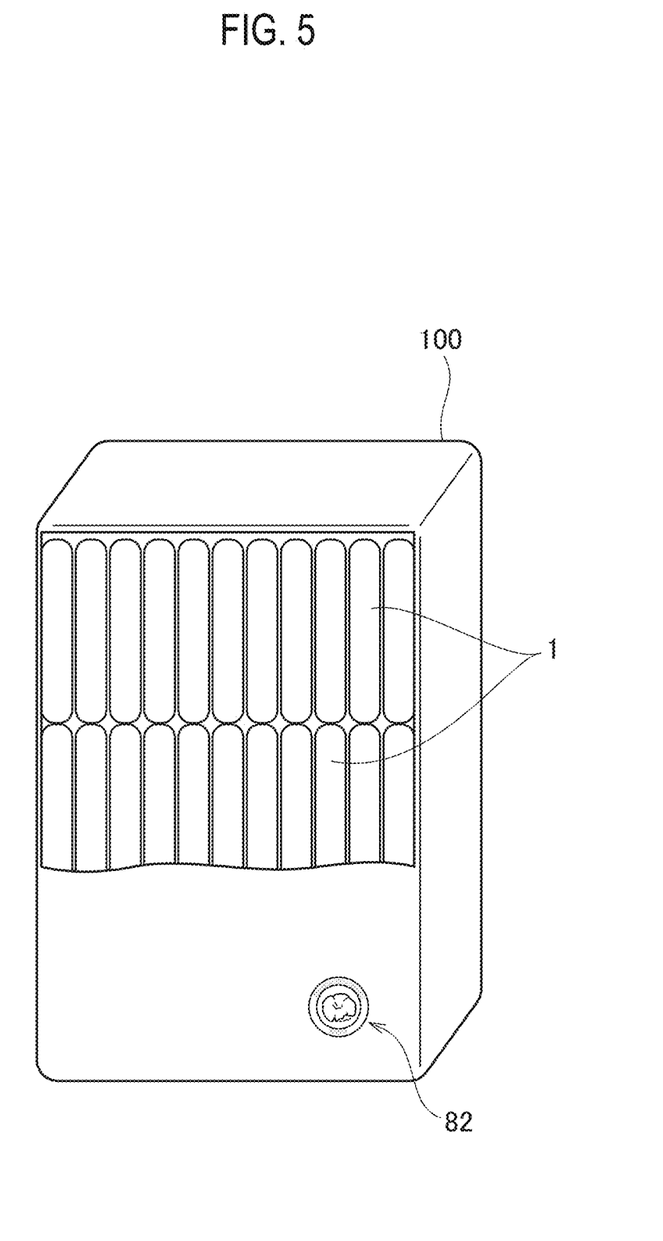
FIG. 5 illustrates a packaging for the absorbent article according to the embodiment.

FIG. 5 is a view illustrating a packaging for the absorbent article according to the embodiment. The packaging includes the absorbent article 1 including the nonwoven fabric and a packaging bag 100 for packaging the absorbent article 1. The structure of the absorbent article 1 is as described above.

The packaging bag 100 stores a plurality of absorbent articles 1. The packaging bag 100 includes a mark 82 for allowing the user to recognize the use of the organic cotton fibers 10. Preferably, each absorbent article 1 also includes a mark 84 for allowing the user to recognize the use of the organic cotton fibers 10. The mark 84 attached to the absorbent article 1 is a mark that gives the user the same recognition as the mark 82 attached to the packaging bag 100. Specifically, the mark 84 attached to the absorbent article 1 may be the same as or similar to the mark 82 attached to the packaging bag 100. The mark 84 attached to the absorbent article 1 may be different from the mark 82 attached to the packaging bag 100 if the user recognizes the use of the organic cotton fibers 10.

The marks 82 and 84 may be marks certified by an external agency certifying the use of organic cotton. In this case, it is possible to improve the reliability that the organic cotton is used, allowing the sense of higher security to be given to the user.

In FIGS. 2 and 5, the same marks 82 and 84 are attached to both the absorbent article 1 and the packaging bag 100. Alternatively, the mark 82 attached to the absorbent article 1 and the mark 84 attached to the packaging bag 80 need to be similar to each other, and may not exactly be the same as each other. In this case, it is also possible to allow the user to recognize the use of the organic cotton fiber.

Thus, in the packaged state of the absorbent articles 1 packaged in the packaging bag 100, the mark 82 attached to the packaging bag 100 allows the user to recognize the use of the organic cotton fiber. In addition, even when the absorbent article 1 is taken out from the packaging bag 100, the mark 84 attached to the absorbent article 1 can explicitly inform the user of the use of the organic cotton fibers. Therefore, it is possible to give the user a sense of security guaranteeing gentleness to the skin.

The plurality of absorbent articles 1 may be individually wrapped in the packaging bag 100. In this case, a mark for allowing the user to recognize the use of the organic cotton fibers may be attached to a packaging material for individually packaging the absorbent article 1.

Although the embodiment of the present invention has been described above in detail, it is apparent for persons who have ordinary skill in the art that the embodiment described in this specification do not limit the scope of the present invention. Changes and modifications may apply to the embodiment of the present invention without departing from the spirit and scope of the present invention that are defined by the description of the appended claims. The description of the present specification, therefore, has been understood to be illustrative and is in no way intended to limit the scope of the invention.

The contents of Japanese Patent Application No. 2016-97495 (filed on May 13, 2016) have been incorporated herein by reference in its entirety.

REFERENCE SIGNS LIST

1 Absorbent article
3 Topsheet
4 Backsheet
7 Absorber
10 Organic cotton fiber
11 Fiber lump
12 Synthetic fiber
82 Mark
84 Mark
100 Packaging bag
300 Colored sheet

The invention claimed is:

1. An absorbent article, comprising:
a nonwoven fabric,
wherein
the nonwoven fabric includes organic cotton fibers,
the organic cotton fibers form a plurality of fiber lumps in the nonwoven fabric,
the fiber lumps are configured to be visible from outside,
a light transmittance of a portion corresponding to the fiber lumps in the nonwoven fabric is lower than a light transmittance of a portion in the nonwoven fabric where the fiber lumps are not present,
the absorbent article further comprises a colored sheet overlapping the nonwoven fabric, and
the colored sheet is provided inside the nonwoven fabric in a thickness direction of the absorbent article.

2. The absorbent article according to claim 1, wherein the plurality of fiber lumps is provided biased toward a surface side of the absorbent article in the thickness direction of the absorbent article.

3. The absorbent article according to claims 1, wherein the nonwoven fabric further includes synthetic fibers, and a region having a density lower than a density of the fiber lumps and a density of the synthetic fibers is formed around the fiber lumps.

4. An absorbent article, comprising:
a nonwoven fabric,
wherein
the nonwoven fabric includes organic cotton fibers,
the organic cotton fibers form a plurality of fiber lumps in the nonwoven fabric,
the fiber lumps are configured to be visible from outside,
a light transmittance of a portion corresponding to the fiber lumps in the nonwoven fabric is lower than a light transmittance of a portion in the nonwoven fabric where the fiber lumps are not present,
a fiber density of the fiber lumps is 0.075 g/cm$^3$ to 0.2 g/cm$^3$,
the absorbent article further comprises a colored sheet overlapping the nonwoven fabric, and
the colored sheet is provided inside the nonwoven fabric in a thickness direction of the absorbent article.

5. An absorbent article, comprising:
a nonwoven fabric,
wherein
the nonwoven fabric includes organic cotton fibers,
the organic cotton fibers form a plurality of fiber lumps in the nonwoven fabric,
the fiber lumps are configured to be visible from the outside,
a light transmittance of a portion corresponding to the fiber lumps in the nonwoven fabric is lower than a light transmittance of a portion in the nonwoven fabric where the fiber lumps are not present, the nonwoven fabric includes synthetic fibers, the organic cotton fibers have an average fiber length shorter than an average fiber length of the synthetic fibers, the absorbent article further comprises a colored sheet overlapping the nonwoven fabric, and the colored sheet is provided inside the nonwoven fabric in a thickness direction of the absorbent article.

6. The absorbent article according to claim 5, wherein the organic cotton fibers are not thermally fused to the synthetic fibers.

* * * * *